United States Patent [19]

Konishi

[11] 4,281,009

[45] Jul. 28, 1981

[54] HYDANTOIN DERIVATIVES

[75] Inventor: Jin-emon Konishi, Musashino, Japan

[73] Assignee: Nippon Zoki Pharmaceutical Co., Ltd., Osaka, Japan

[21] Appl. No.: 939,791

[22] Filed: Sep. 5, 1978

[30] Foreign Application Priority Data

Jun. 13, 1978 [JP] Japan ................... 53-71236

[51] Int. Cl.³ ................. A61K 31/415; C07D 233/30; C07D 213/46
[52] U.S. Cl. ............... 424/273 R; 548/309; 548/314; 546/278; 546/210
[58] Field of Search ............... 548/309, 314; 544/370, 544/139; 546/278, 210; 424/273 R

[56] References Cited

U.S. PATENT DOCUMENTS

2,409,755  10/1946  Henze ................ 548/314
2,711,413  6/1955  Campaigne ................ 548/309

FOREIGN PATENT DOCUMENTS

1135915  9/1962  Fed. Rep. of Germany ........ 548/309

OTHER PUBLICATIONS

Chem. Abs., vol. 85, 1976, 85:103671d.
Chem. Abs., vol. 87, 1977, 87:47851q.
Journal Medicinal Chem.; Novelli, et al.; Jan. 1968, p.177.

*Primary Examiner*—Henry R. Jiles
*Assistant Examiner*—Robert C. Whittenbaugh
*Attorney, Agent, or Firm*—Brisebois & Kruger

[57] ABSTRACT

New hydantoin derivatives, a process for the preparation thereof and pharmaceutical compositions containing the derivatives as active ingredients, particularly remedies for treatment of diseases caused by stress.

22 Claims, 2 Drawing Figures

HYDANTOIN DERIVATIVES

BACKGROUND OF THE INVENTION

The present invention relates to new hydantoin derivatives, a process for the preparation thereof and pharmaceutical compositions containing the derivatives as active ingredients, particularly remedies for treatment of diseases caused by stress.

In the current community of advanced civilization and technology, stress due to human, internal or external causes are increasing. We suffer from various complicated diseases caused by the stress. As the causes of stress, there may be mentioned physical stimuli such as cold, noise and high energy radiation, chemical stimuli such as deficiency in oxygen and chemicals (for example, ACTH and cortisone), biological stimuli such as bacteria and viruses and mental stimuli such as fear, anxiety and fretfulness. Many kinds of diseases are caused by the stress mainly in the autonomic nervous system.

It is well known that if those kinds of stress are not relieved properly by the protective controlling actions of the living body, and they become chronic or they are fixed, there arises secondary adaptation diseases such as hypertension, nephrosclerosis, rheumatism, gastric ulcer and duodenal ulcer.

Selye reported that as adaptation syndromes, the following phenomena arise:
1. hypertrophy of adrenal cortex,
2. atrophy of thymus and lymphatic tissue, and
3. bleeding from the inside wall of the stomach and intestines or ulcer thereof.

Various remedies for relieving the stress which causes the above mentioned diseases have been developed. However, those remedies have disadvantages. For example, meprobamate used as an anti-anxiety agent is accompanied with addiction to drugs to cause convulsion and disturbance of consciousness as abstinence symptoms. Diazepam and chlordiazepoxide have the same disadvantages. Therefore, removing a patient from use of those drugs is a medical problem.

An object of the present invention is to provide a remedy useful for the treatment of diseases caused by stress and free from harmful side-effects.

The compounds relating to the present invention are new hydantoin derivatives having the general formula (I):

in which at least one of $R_1$, $R_2$, and $R_3$ is a group other than hydrogen and $R_1$, $R_2$ and $R_3$ which may be the same or different are hydrogen, halogen, carboxyl, sulfonic acid, alkyl, hydroxyalkyl, haloalkyl or a group of formula $OR_7$ in which $R_7$ is hydrogen, saturated or unsaturated straight chain or branched aliphatic hydrocarbon, aralkyl or alkali metal atom, and X is alkyl, heterocyclic or a group of general formula (II):

in which $R_4$, $R_5$ and $R_6$ which may be the same or different are hydrogen, halogen, carboxyl, sulfonic acid, alkyl, hydroxyalkyl, haloalkyl or a group of formula $OR_7$ ($R_7$ having the same meaning as above).

Among the hydantoin compounds having one or two substituents at the 5-position, 5-ethyl-5-phenylhydantoin, 5,5-diphenylhydantoin (DPH), etc. have been known as anticonvulsants. Particularly, those compounds are used as anti-epilepsy drugs.

After intensive investigations on various hydantoin compounds having substituents at the 5-position, we have found that some 5,5-disubstituted hydantoin compounds having at least one substituted phenyl group at the 5-position have pharmacological effects remarkably effective against diseases caused by stress, particularly, sedative, analgesic, antiulcerogenic, sleep prolongation and antihypertensive effects. It has also been found that the compounds of the present invention act as a sedative on the central nervous system in contrast with DPH which stimulates the central nervous system as anticonvulsants, and the former compounds have pharmacological effects utterly different from those of DPH as will be understood by a study of the pharmacological tests given below.

An object of the present invention is to provide new hydantoin derivatives useful as a remedy for diseases caused by stress.

Another object of the present invention is to provide a process for preparing said derivatives from ketone.

Still another object of the invention is to provide medical compositions comprising said derivatives and at least one pharmaceutically acceptable carrier or diluent.

SUMMARY OF THE INVENTION

The new hydantoin derivatives of the present invention have in their structure at least one substituted phenyl group at the 5-position of hydantoin. Structures of the hydantoin derivatives are shown by the general formula (I). Examples of groups of the compounds of the present invention and selected groups of the compounds preferred from a pharmaceutical viewpoint will be shown below.

In general formula (I), at least one of $R_1$, $R_2$ and $R_3$ is a group other than hydrogen and $R_1$, $R_2$ and $R_3$ which may be the same or different each are hydrogen or another substituent. The substituent may be selected from the group consisting of halogens such as fluorine, chlorine, bromine and iodine; carboxyl groups which may be in the form of a free carboxyl, carboxylic acid salts and carboxylic acid esters; sulfonic acid which may be in the form of a free sulfonic acid, sulfonic acid salts and sulfonic acid esters; straight chain or branched alkyls, particularly those having 1-8 carbon atoms, preferably 1-5 carbon atoms, for example, methyl, ethyl, propyl, isopropyl, butyl, isobutyl, s.-butyl, t.-butyl, pentyl, isopentyl and t.-pentyl groups; monohydroxy-, dihydroxy-, trihydroxy-, tetrahydroxy- and/or other polyhydroxyalkyl groups such as hydroxyalkyl having preferably 1-4 carbon atoms, for example, hydroxymethyl, hydroxyethyl, dihydroxyethyl, hydroxypropyl, dihydroxypropyl, trihydroxypropyl, hydroxybutyl, dihydroxybutyl, trihydroxybutyl and tetrahydroxybutyl groups; haloalkyl groups having one or more halogen atoms such as fluorine, chlorine, bromine and iodine, preferably those having 1-4 carbon atoms such as chloromethyl, bromomethyl, iodomethyl, trifluoromethyl, chloroethyl, bromoethyl, iodoethyl, chloropropyl, bromopropyl, iodopropyl, chlorobutyl, bromobutyl and iodobutyl groups; and groups of the formula $OR_7$.

Groups of the formula $OR_7$ may be selected from the group consisting of hydroxyl in which the hydrogen atoms may be substituted with an alkali metal atom, such as sodium or potassium; groups in which the aliphatic hydrocarbon moiety represents saturated or unsaturated straight chain or branched alkyl, alkenyl or alkynyl, for example, alkoxy groups having 1-8 carbon atoms, preferably 1-4 carbon atoms such as methoxy, ethoxy, propoxy, isopropoxy, butoxy, isobutoxy, s.-butoxy and t.-butoxy groups, alkenyloxy groups having 3-8 carbon atoms, preferably 3-5 carbon atoms such as allyloxy, 2-butene-1-oxy, 3-butene-1-oxy, 3-butene-2-oxy, 4-pentene-1-oxy, 4-pentene-2-oxy and 3-pentene-2-oxy groups and alkynyloxy groups having 3-8 carbon atoms, preferably 3-5 carbon atoms such as propargyloxy, 2-butyne-1-oxy, 3-butyne-2-oxy, 2-pentyne-1-oxy and 2-methyl-3-butyne-2-oxy groups; and substituted or unsubstituted aralkyloxy groups, preferably such as benzyloxy, phenethyloxy and naphthylmethoxy groups.

Another substituent X at the 5-position may be selected from alkyl groups, particularly straight chain or branched alkyl having 1-8 carbon atoms, preferably 1-5 carbon atoms such as methyl, ethyl, propyl, isopropyl, butyl, isobutyl, s.-butyl, t.-butyl, pentyl, isopentyl and t.-pentyl groups.

Substituent X may be a heterocyclic group having one or more hetero-atoms such as nitrogen, sulfur and oxygen. It may be selected from the group consisting of furyl, thienyl, pyrrolyl, pyrrolidinyl, pyrrolidino, pyridyl, piperidyl, piperidino, piperazino and morpholino groups. Particularly, the furyl or thienyl group is preferred.

Further, substituent X may be a group having the formula (II):

(II)

wherein $R_4$, $R_5$ and $R_6$ which may be the same or different each are hydrogen or another substituent. The substituent may be selected from the substituents shown above as $R_1$, $R_2$ and $R_3$. In general formula (I):

When X is an alkyl group, one of $R_1$, $R_2$ and $R_3$ may be preferably a group other than hydrogen, particularly a group of formula $OR_7$, When X is a heterocyclic group, particularly a furyl or a thienyl group, one of $R_1$, $R_2$ and $R_3$ may be a group other than hydrogen, preferably a group of formula $OR_7$, When X is a group of formula (II), When all of $R_4$, $R_5$ and $R_6$ are hydrogen, one of $R_1$, $R_2$ and $R_3$ may be a group other than hydrogen, preferably halogen or a group of formula $OR_7$, One of $R_4$, $R_5$ and $R_6$ and one of $R_1$, $R_2$ and $R_3$ which may be the same or different may be a group other than hydrogen, preferably a group of formula $OR_7$, When one of $R_4$, $R_5$ and $R_6$ is a group of formula $OR_7$, one of $R_1$, $R_2$ and $R_3$ may be a group of formula $OR_7$ and the remaining one of $R_1$, $R_2$ and $R_3$ may be halogen, alkyl, hydroxyalkyl or a group of formula $OR_7$, When one of $R_4$, $R_5$ and $R_6$ is a group of formula $OR_7$, one of $R_1$, $R_2$ and $R_3$ may be a group of formula $OR_7$ and the remaining two of $R_1$, $R_2$ and $R_3$ which may be the same of different may be halogen, alkyl, hydroxyalkyl or a group of formula $OR_7$, Two of $R_4$, $R_5$ and $R_6$ and two of $R_1$, $R_2$ and $R_3$ which may be the same or different may be halogen, carboxyl, alkyl, hydroxyalkyl, haloalkyl or a group of formula $OR_7$, Or $R_1$, $R_2$, $R_3$, $R_4$, $R_5$ and $R_6$ which may be the same or different may be halogen, alkyl or a group of formula $OR_7$.

The new hydantoin derivatives included in the present invention are, for example, the following compounds:

5-Alkyl-5-halogenophenylhydantoins,
5-Alkyl-5-carboxyphenylhydantoins,
5-Alkyl-5-sulfophenylhydantoins,
5-Alkyl-5-alkylphenylhydantoins,
5-Alkyl-5-hydroxyalkylphenylhydantoins,
5-Alkyl-5-haloalkylphenylhydantoins,
5-Alkyl-5-hydroxyphenylhydantoins,
5-Alkyl-5-alkoxyphenylhydantoins,
5-Alkyl-5-alkenyloxyphenylhydantoins,
5-Alkyl-5-alkynyloxyphenylhydantoins,
5-Alkyl-5-aralkyloxyphenylhydantoins,
5-Heterocyclyl-5-halogenophenylhydantoins,
5-Heterocyclyl-5-carboxyphenylhydantoins,
5-Heterocyclyl-5-sulfophenylhydantoins,
5-Heterocyclyl-5-alkylphenylhydantoins,
5-Heterocyclyl-5-hydroxyalkylphenylhydantoins,
5-Heterocyclyl-5-haloalkylphenylhydantoins,
5-Heterocyclyl-5-hydroxyphenylhydantoins,
5-Heterocyclyl-5-alkoxyphenylhydantoins,
5-Heterocyclyl-5-alkenyloxyphenylhydantoins,
5-Heterocyclyl-5-alkynyloxyphenylhydantoins,
5-Heterocyclyl-5-aralkyloxyphenylhydantoins,
5-Furyl-5-halogenophenylhydantoins,
5-Furyl-5-carboxyphenylhydantoins,
5-Furyl-5-sulfophenylhydantoins,
5-Furyl-5-alkylphenylhydantoins,
5-Furyl-5-hydroxyalkylphenylhydantoins,
5-Furyl-5-haloalkylphenylhydantoins,
5-Furyl-5-hydroxyphenylhydantoins,
5-Furyl-5-alkoxyphenylhydantoins,
5-Furyl-5-alkenyloxyphenylhydantoins,
5-Furyl-5-alkynyloxyphenylhydantoins,
5-Furyl-5-aralkyloxyphenylhydantoins,
5-Thienyl-5-halogenophenylhydantoins,
5-Thienyl-5-carboxyphenylhydantoins, 5-Thienyl-5-sulfophenylhydantoins,
5-Thienyl-5-alkylphenylhydantoins,
5-Thienyl-5-hydroxyalkylphenylhydantoins,
5-Thienyl-5-haloalkylphenylhydantoins,
5-Thienyl-5-hydroxyphenylhydantoins,
5-Thienyl-5-alkoxyphenylhydantoins,
5-Thienyl-5-alkenyloxyphenylhydantoins,
5-Thienyl-5-alkynyloxyphenylhydantoins,
5-Thienyl-5-aralkyloxyphenylhydantoins,
5-Halogenophenyl-5-phenylhydantoins,
5-Carboxyphenyl-5-phenylhydantoins,
5-Sulfophenyl-5-phenylhydantoins,
5-Alkylphenyl-5-phenylhydantoins,
5-Hydroxyalkylphenyl-5-phenylhydantoins,
5-Haloalkylphenyl-5-phenylhydantoins,
5-Hydroxyphenyl-5-phenylhydantoins,
5-Alkoxyphenyl-5-phenylhydantoins,
5-Alkenyloxyphenyl-5-phenylhydantoins,
5-Alkynyloxyphenyl-5-phenylhydantoins,
5-Aralkyloxyphenyl-5-phenylhydantoins,
5,5-Bis(halogenophenyl)hydantoins,
5,5-Bis(carboxyphenyl)hydantoins,
5,5-Bis(sulfophenyl)hydantoins,
5,5-Bis(alkylphenyl)hydantoins,
5,5-Bis(hydroxyalkylphenyl)hydantoins,
5,5-Bis(haloalkylphenyl)hydantoins,
5,5-Bis(hydroxyphenyl)hydantoins,
5,5-Bis(alkoxyphenyl)hydantoins,
5,5-Bis(alkenyloxyphenyl)hydantoins,
5,5-Bis(alkynyloxyphenyl)hydantoins,
5,5-Bis(aralkyloxyphenyl)hydantoins,
5-Hydroxyalkylphenyl-5-hydroxyphenylhydantoins,
5-Alkoxyphenyl-5-hydroxyphenylhydantoins,
5-Alkenyloxyphenyl-5-hydroxyphenylhydantoins,
5-Alkynyloxyphenyl-5-hydroxyphenylhydantoins,
5-(Halogeno-hydroxyphenyl)-5-hydroxyphenylhydantoins,
5-(Alkyl-hydroxyphenyl)-5-hydroxyphenylhydantoins,
5-(Hydroxyalkyl-hydroxyphenyl)-5-hydroxyphenylhydantoins,
5-Dihydroxyphenyl-5-hydroxyphenylhydantoins,
5-(Halogeno-alkoxyphenyl)-5-alkoxyphenylhydantoins,
5-(Alkyl-alkoxyphenyl)-5-alkoxyphenylhydantoins,
5-(Hydroxyalkyl-alkoxyphenyl)-5-alkoxyphenylhydantoins,
5-Dialkoxyphenyl-5-alkoxyphenylhydantoins,
5-(Halogeno-alkenyloxyphenyl)-5-alkenyloxyphenylhydantoins,
5-(Alkyl-alkenyloxyphenyl)-5-alkenyloxyphenylhydantoins,
5-(Hydroxyalkyl-alkenyloxyphenyl)-5-alkenyloxyphenylhydantoins,
5-Dialkenyloxyphenyl-5-alkenyloxyphenylhydantoins
5-(Halogeno-alkynyloxyphenyl)-5-alkynyloxyphenylhydantoins,
5-(Alkyl-alkynyloxyphenyl)-5-alkynyloxyphenylhydantoins,
5-(Hydroxyalkyl-alkynyloxyphenyl)-5-alkynyloxyphenylhydantoins,
5-Dialkynyloxyphenyl-5-alkynyloxyphenylhydantoins,
5-(Halogeno-aralkyloxyphenyl)-5-aralkyloxyphenylhydantoins,
5-(Alkyl-aralkyloxyphenyl)-5-aralkyloxyphenylhydantoins,
5-(Hydroxyalkyl-aralkyloxyphenyl)-5-aralkyloxyphenylhydantoins,
5-Diaralkyloxyphenyl-5-aralkyloxyphenylhydantoins,
5-(Dihalogeno-hydroxyphenyl)-5-hydroxyphenylhydantoins,
5-(Dialkyl-hydroxyphenyl)-5-hydroxyphenylhydantoins,
5-[Bis(hydroxyalkyl)-hydroxyphenyl]-5-hydroxyphenylhydantoins,
5-Trihydroxyphenyl-5-hydroxyphenylhydantoins,
5-(Dihalogeno-alkoxyphenyl)-5-alkoxyphenylhydantoins,
5-(Dialkyl-alkoxyphenyl)-5-alkoxyphenylhydantoins,
5-[Bis(hydroxyalkyl)-alkoxyphenyl]-5-alkoxyphenylhydantoins,
5-Trialkoxyphenyl-5-alkoxyphenylhydantoins,
5-(Dihalogeno-alkenyloxyphenyl)-5-alkenyloxyphenylhydantoins,
5-(Dialkyl-alkenyloxyphenyl)-5-alkenyloxyphenylhydantoins,
5-(Dihalogeno-alkynyloxyphenyl)-5-alkynyloxyphenylhydantoins,
5-(Dialkyl-alkynyloxyphenyl)-5-alkynyloxyphenylhydantoins,
5-(Dihalogeno-aralkyloxyphenyl)-5-aralkyloxyphenylhydantoins,
5-(Dialkyl-aralkyloxyphenyl)-5-aralkyloxyphenylhydantoins,
5,5-Bis(carboxy-hydroxyphenyl)hydantoins,
5,5-Bis(alkyl-hydroxyphenyl)hydantoins,
5,5-Bis(hydroxyalkyl-hydroxyphenyl)hydantoins,
5,5-Bis(dihydroxyphenyl)hydantoins,
5,5-Bis(halogeno-alkoxyphenyl)hydantoins,
5,5-Bis(carboxy-alkoxyphenyl)hydantoins,
5,5-Bis(alkyl-alkoxyphenyl)hydantoins,
5,5-Bis(hydroxyalkyl-alkoxyphenyl)hydantoins,
5,5-Bis(haloalkyl-alkoxyphenyl)hydantoins,
5,5-Bis(dialkoxyphenyl)hydantoins,
5,5-Bis(halogeno-alkenyloxyphenyl)hydantoins,
5,5-Bis(carboxy-alkenyloxyphenyl)hydantoins,
5,5-Bis(alkyl-alkenyloxyphenyl)hydantoins,
5,5-Bis(hydroxyalkyl-alkenyloxyphenyl)hydantoins,
5,5-Bis(haloalkyl-alkenyloxyphenyl)hydantoins,
5,5-Bis(dialkenyloxyphenyl)hydantoins,
5,5-Bis(halogeno-alkynyloxyphenyl)hydantoins,
5,5-Bis(carboxy-alkynyloxyphenyl)hydantoins,
5,5-Bis(alkyl-alkynyloxyphenyl)hydantoins,
5,5-Bis(hydroxyalkyl-alkynyloxyphenyl)hydantoins,
5,5-Bis(haloalkyl-alkynyloxyphenyl)hydantoins,
5,5-Bis(dialkynyloxyphenyl)hydantoins,
5,5-Bis(alkyl-aralkyloxyphenyl)hydantoins,
5,5-Bis(hydroxyalkyl-aralkyloxyphenyl)hydantoins,
5,5-Bis(haloalkyl-aralkyloxyphenyl)hydantoins,
5,5-Bis(diaralkyloxyphenyl)hydantoins,
5,5-Bis(trihydroxyphenyl)hydantoins,
5,5-Bis(trialkoxyphenyl)hydantoins, and
5,5-Bis(dialkyl-halogenophenyl)hydantoins.

The compounds of the present invention in which the hydrogen atom of the phenolic hydroxyl group is replaced with an alkali metal atom such as sodium or potassium are also included in the compounds of the present invention.

The present invention further includes pharmaceutical salts of the compounds of the present invention with inorganic or organic cations. As examples of the cations, there may be mentioned alkali metals, such as sodium and potassium, alkaline earth metals, such as calcium and magnesium and amines such as monoethanolamine, diethanolamine, dimethylaminoethanol, N-methylglucagon, tris(hydroxymethyl)aminomethane, piperidine, piperazine and morpholine.

According to the present invention, the compounds of the present invention can be obtained by heating ketones having the general formula (III):

(III)

wherein the symbols have the same meanings as those of the general formula (I), together with at least one cyanide such as sodium cyanide, potassium cyanide, lithium cyanide or calcium cyanide and ammonium carbonate, ammonium hydrogencarbonate or a mixture thereof preferably in a solvent.

Those cyanides and ammonium compounds are preferably used in an excess amount as compared with the ketones in general.

As the solvent to be used, there may be mentioned, for example, methanol, ethanol, propanol, ethyl acetate, dioxane, morpholine, formamide, acetamide or dimethylformamide. If desired, solvent mixtures of them with water or hydrous solvents may also be used.

Heating temperature is generally 40°–200° C. and heating time is 1–100 hours. The temperature and time may be selected suitably according to starting materials and solvent.

Further, the present invention provides a process for introducing a hydroxyl group into the phenyl group at the 5-position of the hydantoin, which process comprises dealkylating or dearalkylating the compounds of the present invention wherein the phenyl group at the 5-position of the hydantoin has an alkoxy group or aralkyloxy group according to a known method per se. This process is especially recommended when various by-products are formed and isolation or purification of the object compound is difficult during the preparation of the object compound from the ketone of formula (III) wherein the phenyl group has hydroxyl group, which is a starting material for preparation of the compound of the present invention. The compound of the present invention can be prepared by forming a compound of the invention from an alkoxy- or aralkyloxy-substituted starting ketone (III) by the above described process and, if necessary, dealkylating or dearalkylating the compound to form a hydroxyl group so as to prepare other compounds of the present invention.

The dealkylation reaction can be carried out in a relatively short period of time by reacting the compound with anhydrous aluminum chloride in a substantially water-free solvent such as benzene or toluene.

The dearalkylation reaction can be carried out by reacting the compound with hydrogen in the presence of a catalyst. For example, the reaction can be carried out by allowing the compound to absorb hydrogen gas in the presence of palladium-carbon in a solvent of dioxane and the like.

The compounds of the present invention can be isolated or purified by usual methods. The object can be attained by reprecipitation and/or recrystallization by using a proper solvent. In addition, proper treatments such as decolorization may be effected. The compounds of the invention thus obtained can be identified by measuring melting points, IR analysis, elementary analysis and the like.

The following examples illustrate the process for preparing compounds of the present invention and they do not limit the invention.

EXAMPLE 1

2.0 Grams of 2-(4-hydroxybenzoyl)thiophene were heated together with 5.3 g of potassium cyanide, 17.1 g of ammonium carbonate, 20 ml. of formamide and 10 ml. of water in a stainless steel bomb with occasional stirring at 120° C. for 72 hours. The reaction liquid was adjusted to pH 4 with concentrated hydrochloric acid and then mixed with water to form precipitates. The precipitates thus formed were washed with water, filtered and extracted with ethanol while they were hot. The extract was heated together with a small amount of active carbon under reflux, filtered while it was hot and then cooled to obtain 2.0 g of 5-(4-hydroxyphenyl)-5-(2-thienyl)hydantoin in the form of white crystals.

EXAMPLE 2

55.3 Grams of 3-chloro-4,4'-dimethoxybenzophenone, 65.1 g of potassium cyanide, 96 g of ammonium carbonate and 94.8 g of ammonium hydrogencarbonate were charged in an autoclave together with 500 ml. of formamide and 100 ml. of water and the whole was heated at 120° C. with stirring for 48 hours. The reaction liquid was made acidic with concentrated hydrochloric acid, mixed with water and allowed to stand in a cool place overnight. The precipitates thus formed were washed with water and filtered out. The filtration residue was dissolved in 80% ethanol-water under heating, decolorized with active carbon and recrystallized from ethanol-chloroform to obtain 40.0 g of 5-(3-chloro-4-methoxyphenyl)-5-(4-methoxyphenyl)hydantoin in the form of white crystals.

EXAMPLE 3

34.5 Grams of 4,4'-dimethoxy-3-methylbenzophenone, 66.7 g of potassium cyanide and 232.2 g of ammonium hydrogencarbonate were heated to 120° C. together with 500 ml. of formamide and 100 ml. of water with stirring in an autoclave. After 72 hours, the reaction liquid was made acidic with concentrated hydrochloric acid, mixed with water and allowed to stand overnight. The precipitates thus formed were filtered out. The precipitates were dissolved in acetone, decolorized by active carbon under heating and recrystallized from hexane-acetone to obtain 22.7 g of 5-(4-methoxy-3-methylphenyl)-5-(4-methoxyphenyl)-hydantoin in the form of white crystals.

EXAMPLE 4

100 Grams of 4,4'-dihydroxybenzophenone, 152.1 g of potassium cyanide and 426.3 g of ammonium carbonate were heated to 120° C. together with 750 ml. of formamide and 150 ml. of water with stirring in an autoclave for 48 hours. The reaction liquid was made acidic with concentrated hydrochloric acid, mixed with water and allowed to stand overnight. The precipitates thus formed were filtered out. The precipitates were decolorized by active carbon and recrystallized from 50% methanol to obtain 111.4 g of 5,5-bis(4-hydroxyphenyl)hydantoin in the form of white crystals.

EXAMPLES 5–28

All of the compounds listed in Table 1 were prepared in substantially the same manner as in Examples 1–4. In the following tables, the term (dec.) stands for "decomposition."

TABLE 1

| Example | Compound of the present invention | M.P. (°C.) | Yield (%) |
|---|---|---|---|
| 1 | 5-(4-Hydroxyphenyl)-5-(2-thienyl)-hydantoin | 287–289 (dec.) | 74.1 |
| 2 | 5-(3-chloro-4-methoxyphenyl)-5-(4-methoxyphenyl)hydantoin | 193–195 | 54.9 |
| 3 | 5-(4-methoxy-3-methylphenyl)-5-(4-methoxyphenyl)hydantoin | 222–224 | 51.9 |
| 4 | 5,5-Bis(4-hydroxyphenyl)hydantoin | 310–312 (dec.) | 83.9 |
| 5 | 5-(4-Fluorophenyl)-5-phenyl-hydantoin | 278–279 | 90.3 |
| 6 | 5-(2-Hydroxyphenyl)-5-phenyl-hydantoin | 290–294 (dec.) | 56.2 |
| 7 | 5-(4-Hydroxyphenyl)-5-phenyl-hydantoin | 313–315.5 | 73.2 |
| 8 | 5,5-Bis(3-hydroxyphenyl)hydantoin | 267–269 (dec.) | 43.0 |
| 9 | 5,5-Bis(2-propoxyphenyl)hydantoin | 201–203 | 49.1 |
| 10 | 5,5-Bis(4-propoxyphenyl)hydantoin | 149–150 | 74.2 |
| 11 | 5-(4-Hydroxyphenyl)-5-(4-methoxyphenyl)hydantoin | 297–298 (dec.) | 61.3 |
| 12 | 5,5-Bis(2-benzyloxyphenyl)-hydantoin | 239–241 | 68.9 |
| 13 | 5,5-Bis(4-methylphenyl)hydantoin | 236–238 | 72.2 |
| 14 | 5-(3,4-Dihydroxyphenyl)-5-(4-hydroxyphenyl)hydantoin | 246–249 (dec.) | 58.6 |
| 15 | 5-(2,4-Dimethoxyphenyl)-5-(4-methoxyphenyl)hydantoin | 215–217 | 54.8 |
| 16 | 5-(3,4-Dimethoxyphenyl)-5-(4-methoxyphenyl)hydantoin | 224–227 | 95.2 |
| 17 | 5,5-Bis(3,4-dihydroxyphenyl)-hydantoin | 265 (dec.) | 15.2 |
| 18 | 5,5-Bis(2,4-Dimethoxyphenyl)-hydantoin | 222.5–224 | 35.2 |
| 19 | 5,5-Bis(3,4-dimethoxyphenyl)-hydantoin | 247.5–248.5 | 71.5 |
| 20 | 5,5-Bis(4-hydroxy-3-hydroxymethylphenyl)hydantoin | 233–234 (dec.) | 8.4 |
| 21 | 5,5-Bis(3-hydroxymethyl-4-methoxyphenyl)hydantoin | 268–271 | 69.6 |
| 22 | 5-(2,3,4-Trimethoxyphenyl)-5-(3,4,5-trimethoxyphenyl)hydantoin | 130–133 (subl.) | 72.2 |
| 23 | 5,5-Bis(3,4,5-trimethoxyphenyl)-hydantoin | 220–223 | 69.7 |
| 24 | 5-Ethyl-5-(4-hydroxyphenyl)-hydantoin | 266–269 | 71.0 |
| 25 | 5-Ethyl-5-(2-hydroxyphenyl)-hydantoin | 218–219 | 32.7 |
| 26 | 5-(3-Fluoro-4-methoxyphenyl)-5-(4-methoxyphenyl)hydantoin | 204–205 | 44.2 |
| 27 | 5-(2-Chloro-4-methoxyphenyl)-5-(4-methoxyphenyl)hydantoin | 151–153 | 25.0 |
| 28 | 5-(3,5-Dichloro-4-methoxyphenyl)-5-(4-methoxyphenyl)hydantoin | 250–251 | 38.8 |

EXAMPLE 29

11.0 Grams of 5,5-bis(2-benzyloxyphenyl)hydantoin (Example 12) were reduced in 150 ml. of dioxane in the presence of 2 g of palladium-carbon catalyst in an autoclave under a hydrogen pressure of 10 Kg/cm$^2$ at room temperature. After completion of the hydrogen absorption, the whole was heated at 80° C. under a hydrogen pressure of 10 Kg/cm$^2$ for about 5 hours. The reaction liquid was subjected to filtration to remove the catalyst and concentrated under reduced pressure and the resulting precipitates were filtered out. The product was recrystallized from a mixture of acetone-chloroform to obtain 3.4 g of 5,5-bis(2-hydroxyphenyl)hydantoin in the form of white crystals.

EXAMPLE 30

9.8 Grams of 5-(4-methoxy-3-methylphenyl)-5-(4-methoxyphenyl)hydantoin (Example 3) were suspended in 600 ml. of toluene. The resulting suspension was mixed with 40.0 g of anhydrous aluminum chloride, heated to 80° C. and stirred for 3 hours. The reaction liquid was allowed to cool and poured into a mixture of diluted hydrochloric acid and ice and then diluted with benzene. The resulting precipitates were washed and dissolved in methanol. The solution was heated together with active carbon and filtered while it was hot. The filtrate was mixed with water and allowed to stand quietly in a cool place to precipitate 5-(4-hydroxy-3-methylphenyl)-5-(4-hydroxyphenyl)-hydantoin in the form of white granular crystals. The crystals were filtered out and dried. Yield 7.5 g.

EXAMPLES 31–36

The compounds in Table 2 were prepared in substantially the same manner as in Example 30.

TABLE 2

| Example | Compound of the present invention | M.P. (°C.) | Yield (%) |
|---|---|---|---|
| 29 | 5,5-Bis(2-hydroxyphenyl)hydantoin | 242 (dec.) | 50.7 |
| 30 | 5-(4-Hydroxy-3-methylphenyl)-5-(4-hydroxyphenyl)hydantoin | 288–290 (dec.) | 93.3 |
| 31 | 5-(2,4-Dihydroxyphenyl)-5-(4-hydroxyphenyl)hydantoin | 229–231 | 51.4 |
| 32 | 5-(3,4-Dihydroxyphenyl)-5-(4-hydroxyphenyl)hydantoin | 248–249 (dec.) | 95.8 |
| 33 | 5-(3-Chloro-4-hydroxyphenyl)-5-(4-hydroxyphenyl)hydantoin | 306 (dec.) | 86.2 |
| 34 | 5,5-Bis(2,4-dihydroxyphenyl)-hydantoin | 214–216 (dec.) | 7.4 |
| 35 | 5,5-Bis(3,4-dihydroxyphenyl)-hydantoin | 266 (dec.) | 65.5 |
| 36 | 5,5-Bis(3,4,5-trihydroxyphenyl)-hydantoin | 308 (dec.) | 91.2 |

The results of pharmacological tests of the compounds of the present invention will be shown below. The compounds are represented by the number of the examples given above.

I. Acute toxicity test:

Toxicity tests were carried out by intraperitoneal administration of the compound of the present invention to groups each comprising 10 ICR-strain mice and SD-strain rats. LD$_{50}$ was calculated by the Litchfield-Wilcoxon method based on the number of death 72 hours after the administration. Some of the results are shown in Table 3.

TABLE 3

| | LD$_{50}$ (mg/Kg) | | | |
|---|---|---|---|---|
| | Mice | | Rats | |
| Compound | ♂ | ♀ | ♂ | ♀ |
| 1[a] | >3,000 | 2,000–3,000 | >3,000 | >3,000 |
| 2[a] | 1,000 | 920 | 1,600 | 1,540 |
| 3[a] | >5,000 | >5,000 | >5,000 | >5,000 |
| 4[a] | 1,060 | 980 | 1,370 | 1,320 |
| 5 | 840 | 810 | 1,180 | 1,100 |
| 6[a] | >5,000 | >5,000 | >5,000 | >5,000 |
| 7[a] | >5,000 | >5,000 | >5,000 | >5,000 |
| 8 | 1,350 | 1,270 | 1,800 | 1,660 |
| 9 | >5,000 | >5,000 | >5,000 | >5,000 |
| 10 | 3,600 | 3,460 | 4,000 | 3,800–4,000 |
| 11 | >3,000 | 3,000 | >5,000 | >5,000 |
| 12 | >5,000 | >5,000 | >5,000 | >5,000 |
| 13 | >5,000 | >5,000 | >5,000 | >5,000 |
| 14 | 1,280 | 1,200 | 1,500 | 1,480 |
| 15 | >5,000 | >5,000 | >5,000 | >5,000 |
| 16 | >5,000 | >5,000 | >5,000 | >5,000 |
| 17 | 1,500–2,000 | 1,800 | 2,400 | 2,220 |
| 18 | >5,000 | >5,000 | >5,000 | >5,000 |
| 19 | >5,000 | >5,000 | >5,000 | >5,000 |

TABLE 3-continued

| Compound | LD₅₀ (mg/Kg) | | | |
|---|---|---|---|---|
| | Mice ♂ | Mice ♀ | Rats ♂ | Rats ♀ |
| 20 | >3,000 | 2,980 | 4,310 | 4,090 |
| 21 | >5,000 | >5,000 | >5,000 | >5,000 |
| 22 | >5,000 | >5,000 | >5,000 | >5,000 |
| 23 | >5,000 | >5,000 | >5,000 | >5,000 |
| 24[a] | >5,000 | >5,000 | >5,000 | >5,000 |
| 25[a] | 1,230 | 1,040 | 1,600 | 1,480 |
| 29 | 1,600–1,800 | 1,600 | 1,980 | 1,900 |
| 30[a] | >5,000 | >5,000 | >5,000 | >5,000 |
| 31 | 1,220 | 1,200 | 1,540 | 1,510 |
| 33[a] | >5,000 | >5,000 | >5,000 | >5,000 |
| 34 | >1,000 | 1,200 | 2,000–3,000 | 2,000–3,000 |
| 36 | 820 | 780 | 1,320 | 1,020 |

Note:
[a] All LD$_{50}$ values of respective compounds of the present invention given perorally or subcutaneously to mice (male and female) and rats (male and female) were above 5,000 mg/Kg.

II. Pharmacological tests:

Pharmacological effects of the compounds of the present invention were tested by using rats and mice.

SART stress animals used in the tests described below were raised according to a method of Kita, et al. [Folia Pharmacol. Japan.: 71, 195–210 (1975)]. The SART stress animals raised by said method exhibit a severe stress condition such as decrease in body weight, increase of heart rate and elongation of QRS-time, and, therefore, they can be regarded to be animal models exhibiting human-like autonomic ataxia caused by rapid temperature change.

1. Inhibitory effects on decrease in body weight of stress animals:

Groups of mice each comprising 11–15 dd-strain male mice were divided into the following three groups and the inhibitory effect of the compounds of the present invention on decrease in body weight of the SART stress mice were examined.

Group A: The mice were raised under normal environmental conditions and 10 ml./kg of isotonic sodium chloride solution or 0.5% Tween 80 (registered trademark) was given intraperitoneally once a day.

Group B: The mice were raised under SART stress conditions and 10 ml./Kg of isotonic sodium chloride solution or 0.5% Tween 80 was given intraperitoneally once a day, and Group C: The mice were raised under SART stress conditions and isotonic sodium chloride solution or 0.5% Tween 80 containing a compound of the present invention or another comparative drug prepared in such a way that a dosage would be 10 ml/Kg was given intraperitoneally once a day.

Figure 1:
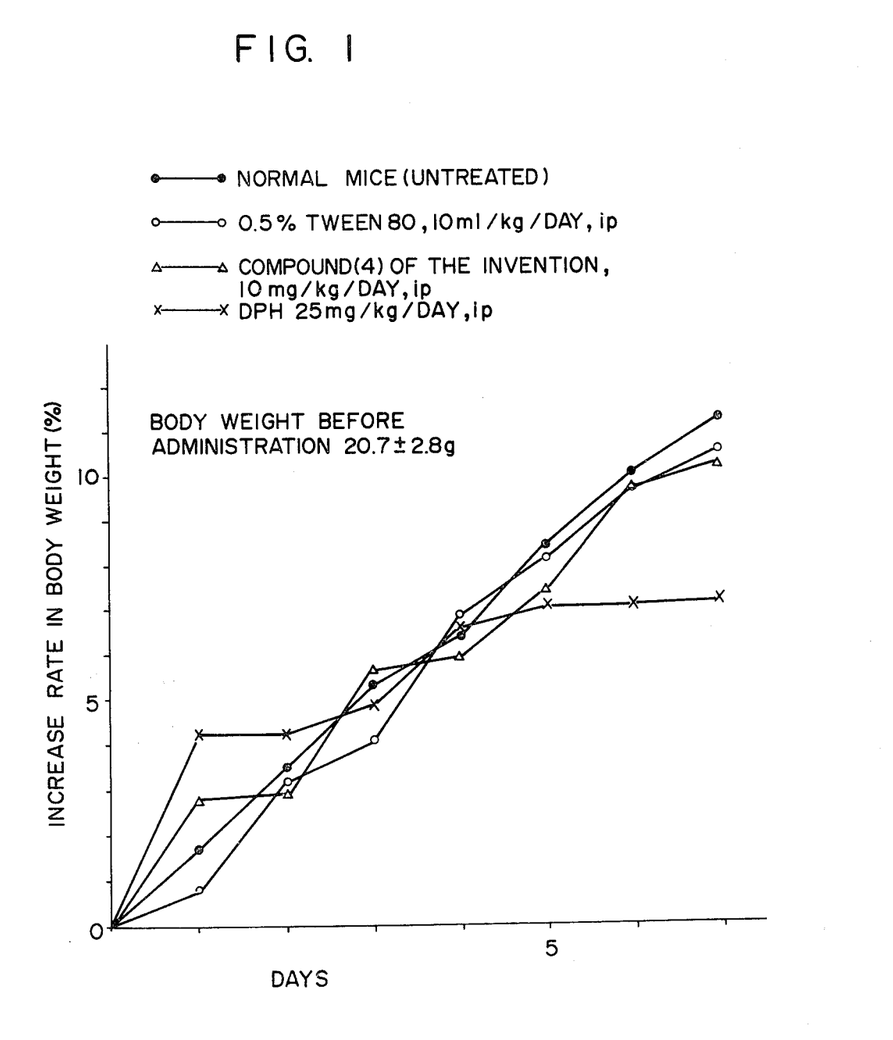
FIG. 1 is a graph showing the effect of a compound of the present invention on increase in body weight of normal mice.
Figure 2:
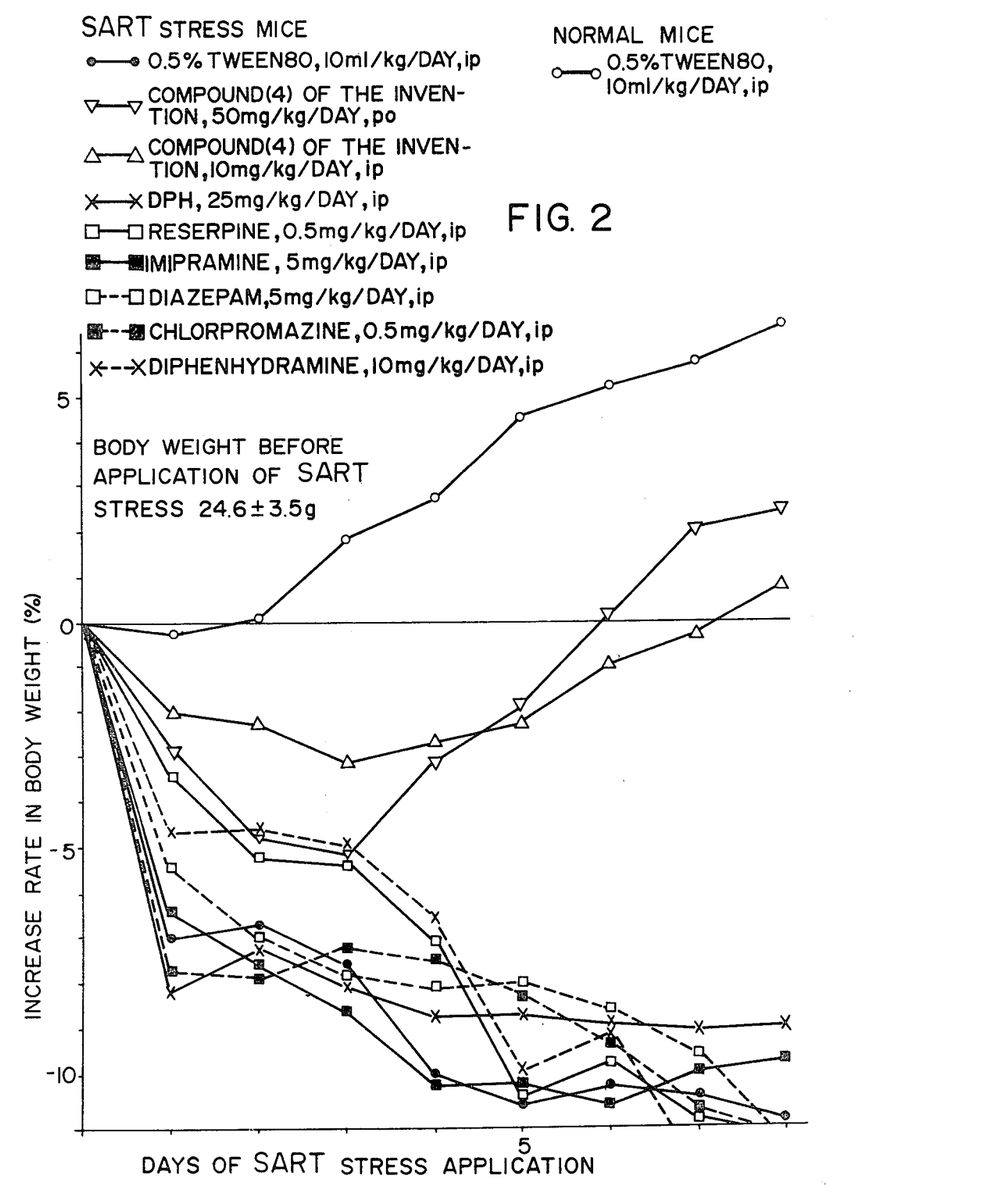
FIG. 2 is a graph showing the effect of a compound of the present invention on decrease in body weight of SART stress mice.

Examples of the results are shown in Table 4 and in FIG. 1 and FIG. 2.

It is apparent in these results that as compared with the normal mice, the SART stress mice exhibited a remarkable decrease in body weight. The compounds of the present invention greatly prevented the decrease and even an inclination of increase in body weight was observed, whereas anti-stress agents such as major tranquilizers, minor tranquilizers and antidepressives did not inhibit the decrease in body weight at all.

No substantial difference in amount of feed intake was observed in the animals in said three groups.

TABLE 4

| Compound | Dosage (mg/kg/day) | Inhibitory effects on decrease in body weight of SART stress mice* |
|---|---|---|
| 1 | 10 | + |
| 2 | 5 | + |
|  | 10 | ++ |
| 3 | 10 | + |
| 4 | 5 | ++ |
|  | 10 | +++ |
| 7 | 10 | ++ |
| 24 | 5 | + |
|  | 10 | ++ |
| 30 | 10 | + |
| 36 | 10 | ++ |
| DPR | 10 | — |
|  | 25 | — |
| Major-tranquillizers | | |
| Reserpine | 0.1 | — |
|  | 0.5 | — |
| Chlorpromazine | 0.1 | — |
|  | 0.5 | — |
| Carpipramine | 5 | — |
|  | 10 | — |
| Antidepressives | | |
| Imipramine | 5 | — |
|  | 10 | — |
| Minor-tranquillizers | | |
| Diazepam | 5 | — |
| Meprobamate | 5 | — |
| Diphenhydramine | 10 | — |

In Table 4 the symbols have the following meaning:
* — No inhibiton effect
+ Inhibition effect was observed
++ Clear inhibition effect was observed
+++ Remarkable inhibition effect or inclination of increase in body weight was observed.

2. Inhibitory effects on increase of heart rate and elongation of QRS-time in stress animals:

Groups of mice each comprising 11 or 12 dd-strain male mice were divided into three groups in the same manner as above and heart rate and QRS-time were determined on the 9th day after initiation of the tests. Examples of the results are shown in Table 5.

The test results indicate that the compounds of the present invention inhibit the increase of the heart rate and elongation of the QRS-time caused by SART stress.

TABLE 5

| Mice | Compound | Dosage (/kg/day) | Heart rate (/min)* | QRS-time (1/1000 sec)* |
|---|---|---|---|---|
| normal | Isotonic sodium** | 10 ml | 657 ± 70 | 11.5 ± 0.5 |
| Isotonic SART stress | sodium** | 10 ml | 773 ± 36 | 15.0 ± 1.6 |
| " | 1 | 100 mg | 741 ± 39 | 13.9 ± 0.8 |
| " | 2 | 50 mg | 698 ± 42 | 12.9 ± 0.8 |
| " | 3 | 100 mg | 710 ± 83 | 13.1 ± 1.7 |
| " | 4 | 37.5 mg | 683 ± 61 | 12.2 ± 0.8 |
| " | 7 | 50 mg | 690 ± 56 | 12.6 ± 1.5 |
| " | 24 | 100 mg | 729 ± 58 | 13.3 ± 0.9 |
| " | 30 | 100 mg | 731 ± 71 | 13.4 ± 1.1 |
| " | 36 | 100 mg | 737 ± 65 | 13.8 ± 1.2 |

*Average ± S.D.
**chloride solution

3. Effect of recovering acetylcholine (Ach) sensitivity of isolated intestinal tract:

Groups each comprising at least 10 dd-strain male mice were used. The compounds of the present invention or other comparative drugs were given intraperitoneally once a day during the stress-causing operation.

On the 6th day, Ach ($10^{-7}$ g/ml.) sensitivity of isolated duodenum was examined using the Magnus method.

Some of the results thus obtained are shown in Table 6.

In Table 6, it is recognized that Ach sensitivity of the isolated duodenum in SART stress mice is declined considerably as compared with that of normal mice. By using the compounds of the present invention, Ach sensitivity of the isolated duodenum in SART stress mice is recovered substantially to a normal value.

TABLE 6

| Mouse | Compound | Dosage (mg/kg/day) | Ach-induced contraction of the isolated deodedum (%)* |
|---|---|---|---|
| Normal | — | — | 100 |
| SART stress | — | — | 28 ± 3 |
| " | 2 | 10 | 80 ± 13 |
| " | 4 | 5 | 61 ± 16 |
| | | 10 | 95 ± 10 |
| " | 36 | 10 | 83 ± 8 |
| " | Reserpine | 0.1 | 75 ± 10 |
| | | 0.5 | 104 ± 15 |
| " | Chlorpromazine | 0.1 | 45 ± 12 |
| | | 0.5 | 81 ± 17 |
| " | Carpipramine | 5 | 52 ± 6 |
| | | 10 | 110 ± 26 |
| " | Imipramine | 5 | 44 ± 15 |
| | | 10 | 100 ± 4 |
| " | Diazepam | 5 | 25 ± 6 |
| " | Meprobamate | 5 | 31 ± 2 |
| " | Diphenhydramine | 10 | 25 ± 5 |

(* : Average ± S.E.)

4. Sedative effect:

4.1 Inhibitory effect on spontaneous motor activities:

Groups each comprising 8-16 dd-strain male mice were used. The compounds of the present invention were given intraperitoneally. After 60 minutes, spontaneous motor activities for 15 minutes were measured by the Animex method.

4.2. Inhibitory effect on exploratory movements:

Groups each comprising 16-35 dd-strain male mice were used. The compounds of the present invention were given intraperitoneally. After 60 minutes, exploratory movements for 15 minutes were measured with an exploratory movement recorder by a method of Tokyo Kyoiku University.

Some of the results of the spontaneous motor activities tests and the exploratory movements tests are shown in Table 7.

The compounds of the present invention exhibited a significant sedative effect.

TABLE 7

| Compound | Dosage (mg/kg) | Inhibitory effect on spontaneous motor activities (%) | Inhibitory effect on exploratory movements (%) |
|---|---|---|---|
| 1 | 50 | 22.4 | — |
| | 150 | 30.7 | 33.2 |
| 2 | 50 | 39.8 | 29.0 |
| | 100 | 50.1 | 38.8 |
| | 125 | 56.3 | 47.8 |
| 4 | 50 | 42.4 | 30.1 |
| | 75 | 52.2 | — |
| | 100 | 61.4 | 54.5 |
| | 125 | — | 61.3 |
| 36 | 50 | 37.8 | 30.6 |
| | 100 | 49.1 | 36.7 |

5. Analgesic effect:

5.1 Tail pressure method:

Randall-Selitto's device for determining analgesic effect by pressure stimulation was used. Groups each comprising 7-13 ddY-strain male normal mice and 7-13 ddY-strain male SART stress mice to which SART stress was applied for at least 4 days were used. The compounds of the present invention or other comparative drugs were given thereto and analgesic effect was determined. The effect was judged by measuring pressure applied 60 minutes after the intraperitoneal administration of the compounds of the present invention. The pressure thus measured was divided by a pressure before the administration. The value thus obtained was compared with that of a control group (to which 10 ml./Kg of 0.5% sodium salt of carboxymethylcellulose or 0.5% Tween 80 was given). When the compounds of the present invention were given perorally and other comparative drugs were given, an average of the pressure at 30, 60, 90 and 120 minutes after the administration was employed for evaluating the effect. Some of the results are shown in Table 8.

When the compounds of the present invention were given perorally, an apparent persistent effect was observed.

TABLE 8

| Compound | Route of administration | Dosage (mg/kg) | Analgesic effect (%) Normal mice | Analgesic effect (%) SART stress mice |
|---|---|---|---|---|
| 1 | Intraperitoneal | 100 | 26.9 | 82.3 |
| 2 | Intraperitoneal | 50 | 54.6 | 79.6 |
| | Intraperitoneal | 100 | 90.7 | 139.0 |
| 3 | Intraperitoneal | 50 | 44.3 | 60.3 |
| | Intraperitoneal | 100 | 47.4 | 91.0 |
| 4 | Intraperitoneal | 50 | 36.1 | 88.2 |
| | Intraperitoneal | 100 | 41.6 | 161.8 |
| 5 | Intraperitoneal | 100 | 19.8 | 95.0 |
| 6 | Intraperitoneal | 100 | 38.1 | 62.7 |
| 7 | Intraperitoneal | 50 | 31.5 | 76.5 |
| | Intraperitoneal | 100 | 38.1 | 106.5 |
| 8 | Intraperitoneal | 100 | 22.9 | 54.7 |
| 9 | Intraperitoneal | 200 | 21.3 | 74.4 |
| 14 | Intraperitoneal | 50 | 35.2 | 78.3 |
| | Intraperitoneal | 100 | 42.6 | 102.2 |
| 23 | Intraperitoneal | 100 | 38.1 | 66.0 |
| 24 | Intraperitoneal | 200 | 20.4 | 31.2 |
| 25 | Intraperitoneal | 200 | 35.5 | 49.0 |
| 30 | Intraperitoneal | 50 | 12.4 | 43.6 |
| | Intraperitoneal | 100 | 59.8 | 97.5 |
| 33 | Intraperitoneal | 100 | 29.5 | 69.8 |
| 36 | Intraperitoneal | 50 | 44.0 | 120.5 |
| | Intraperitoneal | 100 | 67.0 | 180.3 |
| 2 | Peroral | 100 | 37.3 | 70.0 |
| " | " | 160 | 50.2 | 88.2 |
| 4 | " | 50 | 38.8 | 56.8 |

TABLE 8-continued

| Compound | Route of administration | Dosage (mg/kg) | Analgesic effect (%) Normal mice | SART stress mice |
|---|---|---|---|---|
|  | " | 100 | 52.3 | 67.3 |
|  | " | 160 | 68.2 | 90.5 |
| 36 | " | 50 | 40.3 | 63.3 |
|  | " | 100 | 49.9 | 101.7 |
| DPH | Intraperitoneal | 100 | −33.1 | 18.4 |
|  | Peroral | 500 | 5.9 | 17.9 |
| Aminopyrine | Peroral | 100 | 43.5 | 58.9 |
| Morphine | Subcutaneous | 2.0 | 27.1 | 97.9 |

5.2. Acetic acid writhing method:

0.1 ml./10 g of isotonic sodium chloride solution containing 0.7% acetic acid was given intraperitoneally to groups of mice each comprising 5 normal mice and 5 SART stress mice to which SART stress had been applied for 8 days. Writhing syndromes number appeared for 15 minutes after the administration was measured. The effect was evaluated by giving 100 mg/Kg of the compounds of the present invention or DPH subcutaneously and comparing the writhing syndromes number of the mice with that of control mice.

Some of the results are shown in Table 9.

TABLE 9

| Compound | Analgesic effect (%) Normal mice | SART stress mice |
|---|---|---|
| 1 | 2.4 | 20.9 |
| 2 | 4.4 | 27.1 |
| 3 | 2.0 | 22.0 |
| 4 | 4.8 | 33.6 |
| 7 | 3.8 | 31.3 |
| 14 | 5.0 | 36.2 |
| 25 | 1.9 | 19.8 |
| 30 | 3.9 | 25.2 |
| 36 | 8.2 | 29.4 |
| DPH | −16.3 | −6.0 |

5.3. D'Amour-Smith method:

Groups each comprising 10 ddY-strain male normal mice and SART stress mice to which SART stress had been applied for 4 days were used. The root of the tail of the mouse to which black ink was applied was irradiated with infrared rays for up to 15 seconds. Time required till escape response was observed was measured. The effect was shown by the ratio of the mice in which an average value of the response time at 30, 60, 90 and 120 minutes after the administration of the compounds of the present invention or other comparative drugs was prolonged to at least 2 times as long as the time before the administration.

Some of the results are shown in Table 10.

TABLE 10

| Compound | Route of administration | Dosage (mg/kg) | Analgesic effect (%) Normal mice | SART stress mice |
|---|---|---|---|---|
| 1 | Intraperitoneal | 200 | 20 | 30 |
| 2 | Intraperitoneal | 100 | 30 | 50 |
| 3 | Intraperitoneal | 100 | 30 | 40 |
| 4 | Intraperitoneal | 100 | 40 | 60 |
| 5 | Intraperitoneal | 100 | 10 | 40 |
| 7 | Intraperitoneal | 100 | 40 | 50 |
| 14 | Intraperitoneal | 100 | 30 | 60 |
| 23 | Intraperitoneal | 200 | 20 | 40 |
| 30 | Intraperitoneal | 100 | 20 | 30 |
| 33 | Intraperitoneal | 100 | 20 | 30 |
| 36 | Intraperitoneal | 100 | 40 | 60 |
| 2 | Peroral | 100 | 10 | 30 |
|  | " | 160 | 30 | 60 |
| 4 | " | 50 | 10 | 40 |
|  | " | 100 | 20 | 50 |
|  | " | 160 | 40 | 60 |
| 36 | " | 100 | 20 | 30 |
|  | " | 160 | 30 | 40 |
| DPH | " | 500 | 0 | 0 |
| Aminopyrine | " | 100 | 10 | 50 |
| Morphine | Subcutaneous | 0.3 | 10 | 20 |

5.4 Method of measuring a pain induced by Bradykinin:

Groups each comprising 4–8 SD-strain male normal rats and SART stress rats to which SART stress had been applied for 4 days were used. The tests were carried out according to the method of Deffenu et al. [Deffenu, G., Pegrassi, L., & Fumachi. B.; J. Pharm. Pharmacol.; 18, 135 (1966)] and Blane method [Blane, G. F.; J. Pharm. Pharmacol.; 19, 367 (1967)]. The effect judged was shown by ratio of the rats in which the effect was recognized according to the method of Abe, et al. [Abe, Kaneko & Takagi; Folia Pharmacol. Japon.; 67, 9–14 (1971)].

Some of the results are shown in Table 11.

TABLE 11

| Compound | Route of Administration | Dosage (mg/kg) | Analgesic effect (%) Normal rats | SART stress rats |
|---|---|---|---|---|
| 2 | Intraperitoneal | 100 | 66.7 | 75 |
| 4 | Intraperitoneal | 100 | 100 | 100 |
| 7 | Intraperitoneal | 100 | 50 | 66.7 |
| 24 | Intraperitoneal | 100 | 20 | 50 |
| 36 | Intraperitoneal | 100 | 33.3 | 50 |
| 2 | Peroral | 100 | 10 | 30 |
| 4 | " | 100 | 0 | 40 |
| 36 | " | 100 | 10 | 33.3 |
| DPH | " | 500 | 0 | 0 |
| Morphine | Subcutaneous | 2.5 | 33.3 | 50 |

6. Antiulcerogenic effect:

6.1 Antiulcerogenic effect on Takagi's restraint-plus-water-immersing ulcer:

Groups each comprising 8–26 dd-strain male mice were used. The tests were carried out according to a method of Takagi, et al. [Chem. Pharm. Bull.; 12, 465 (1964)]. Sum of length of diseased parts in the glandular stomach was measured and it was compared with that of control group. The compounds of the present invention or DPH was given intraperitoneally immediately before the restraint and immersion in water.

Some of the results are shown in Table 12.

TABLE 12

| Compound | Dosage (mg/kg) | Antiulcerogenic effect on Takagi's restraint-plus-water-immersing ulcer (%) |
|---|---|---|
| 1 | 150 | 30.6 |
| 2 | 75 | 15.4 |
|   | 150 | 36.6 |
| 4 | 25 | 14.2 |
|   | 75 | 39.1 |
|   | 125 | 53.0 |
| 5 | 150 | 22.8 |
| 24 | 75 | 11.9 |
|   | 125 | 27.5 |
| 33 | 150 | 29.8 |
| 36 | 125 | 31.2 |
| DPH | 50 | 7.8 |
|   | 100 | 9.0 |

6.2. Antiulcerogenic effect on Shay's ulcer (operative ulcer):

Tests were carried out by using groups of rats each comprising 5-10 Wistar-strain male rats according to Shay method [Shay Harry; Gastroenterology,; 5, 43 (1945)]. Ulcers in the anterior stomach were classified on the following basis:

0. no disease,
1. bleeding or erosion,
2. 1-5 small ulcers (diameter of less than 3 mm)
3. 6 or more small ulcers or one big ulcer (diameter of more than 3 mm)
4. two or more big ulcers
5. perforating ulcer The compounds of the present invention were given intraperitoneally 10 times and atropine known as antiulcerogenic agent was given intraperitoneally 7 times in total over two days before the ligation of pylorus.

Some of the results are shown in Table 13.

TABLE 13

| Compound | Dosage (mg/kg) | Antiulcerogenic effect on Shay's ulcer (operative ulcer)(%) |
|---|---|---|
| 1 | 100 | 14.6 |
|   | 150 | 26.5 |
| 2 | 100 | 23.4 |
|   | 150 | 29.3 |
| 4 | 25 | 26.4 |
|   | 50 | 38.0 |
|   | 100 | 50.0 |
|   | 150 | 64.8 |
| 5 | 150 | 20.7 |
| 24 | 50 | 17.5 |
|   | 100 | 32.2 |
| 33 | 150 | 54.2 |
| 36 | 100 | 30.1 |
|   | 150 | 43.9 |
| Atropine | 3 | 29.3 |
|   | 6 | 7.3 |

7. Effect of prolongation of sleeping time:

Groups of mice each comprising 10 ddY-strain male mice were used. Sodium salt of hexobarbital was given intraperitoneally. Thereafter, the period of time in which righting reflex disappeared was measured. The effect was evaluated on the basis of prolongation of time of disappearance of righting reflex by the intraperitoneal administration of the compounds of the present invention as compared with control mice.

Some of the results are shown in Table 14.

TABLE 14

| Compound | Dosage (mg/kg) | Effect of prolongation of sleeping time (%) |
|---|---|---|
| 1 | 100 | 36.9 |
| 2 | 100 | 55.9 |
|   | 300 | 248.5 |
| 3 | 100 | 76.6 |
|   | 300 | 93.9 |
| 4 | 20 | 37.2 |
|   | 50 | 84.4 |
|   | 100 | 123.6 |
| 5 | 100 | 31.0 |
|   | 300 | 38.1 |
| 6 | 100 | 30.6 |
|   | 300 | 33.7 |
| 7 | 20 | 48.0 |
|   | 50 | 101.7 |
|   | 100 | 112.3 |
| 8 | 100 | 16.9 |
| 9 | 50 | 10.5 |
|   | 300 | 39.0 |
| 10 | 50 | 17.0 |
| 13 | 300 | 14.1 |
| 14 | 100 | 20.2 |
| 15 | 100 | 15.4 |
|   | 300 | 23.9 |
| 16 | 300 | 20.8 |
| 19 | 100 | 10.0 |
| 21 | 100 | 25.1 |
| 22 | 100 | 13.1 |
| 23 | 100 | 19.9 |
|   | 300 | 22.6 |
| 24 | 50 | 42.1 |
|   | 100 | 54.4 |
|   | 300 | 84.4 |
| 25 | 300 | 55.4 |
| 30 | 100 | 26.6 |
|   | 300 | 97.4 |
| 31 | 100 | 19.1 |
| 33 | 100 | 24.2 |
|   | 300 | 32.9 |
| 36 | 100 | 11.3 |
|   | 300 | 46.7 |

8. Antihypertensive effect:

Groups of rats each comprising 6-9 spontaneously hypertensive rats (SHR) were used. The compounds of the present invention or DPH was given intraperitoneally. The rate of antihypertension 60 minutes after the administration was determined.

Some of the results are shown in Table 15.

TABLE 15

| Compound | Dosage (mg/Kg) | Rate of antihypertension (%) |
|---|---|---|
| 2 | 150 | 22.4 |
| 4 | 100 | 21.5 |
|   | 150 | 34.1 |
|   | 300 | 45.7 |
| 30 | 150 | 10.9 |
|   | 300 | 28.6 |
| 36 | 150 | 19.8 |
| DPH | 150 | 6.6 |

9. Inhibitory effect on Tremorine-induced tremor:

Groups of mice each comprising 10-40 dd-strain male mice were used. Effect of the compounds of the present invention on tremor caused by tremorine was examined. The compounds of the present invention or DPH was given intraperitoneally. 45 minutes thereafter, 10 mg/Kg of tremorine was given intraperitoneally for inducing the tremor. The mice were observed to know whether the tremor was induced or not during the time from immediately after the administration till 30 minutes thereafter.

Some of the results are shown in Table 16.

As compared with the control group, time till appearance of tremor was prolonged significantly in the groups to which the compounds of the present invention were given.

The results of the tests indicate that the compounds of the present invention can be used as a remedy or a supplementary remedy for the treatment of writer's cramp or Parkinson's disease.

It was confirmed in the tests that by the intraperitoneal administration of 10 mg/Kg of tremorine, diarrhea appeared in the mice in addition to the tremor. However, in the groups to which the compounds of the present invention were given, the diarrhea was relieved.

TABLE 16

| Compound | Dosage (mg/kg) | Inhibitory effect on Tremorine-induced tremor (%) |
|---|---|---|
| 1 | 150 | 33 |
| 2 | 100 | 38 |
| 4 | 100 | 54 |
| 7 | 100 | 35 |
| 24 | 150 | 40 |
| 33 | 100 | 29 |
| DPH | 50 | 0 |
|  | 100 | 0 |

As apparently shown by the results of the above toxicity and pharmacological tests, the compounds of the present invention are characterized by their low toxicity and broad pharmacological effects, particularly relief of stress conditions and prevention, improvement or treatment of various diseases caused by stress. Thus, the compounds of the present invention and pharmaceutically acceptable salts thereof can be expected to have medical uses not only as sedative, analgesic, antiulcerogenic agent, hypnotic or antihypertensive drug, but also as remedies, supplementary remedies or preventive medicines for the treatment of various diseases caused by stress, for example, nervous, muscular and skeletal diseases such as general malaise syndrome, cold constitution, motion sickness, sleeplessness, neuralgia, paresthesia, chronic articular rheumatism, articular pain, back pain, low back pain, muscular convulsion, tremor, writer's cramp and cervical vertebral syndrome; circulating system diseases such as cardiac neurosis, stenocardia, essential hypertension, hypotension syndrome, and migraine; digestive system diseases such as chronic gastritis, hyperacidity, pyrosis, nervous vomiting, pylorospasm, peptic ulcer, ulcerative colitis, chronic constipation, hypersensitive large intestine and anorexia nervosa; diseases of internal secretion and metabolism systems such as menstrual disorder, obesity, diabetes mellitus, chronic fatigue and hyperthyroidism; diseases of urinary organs and genital organs such as dysuria, neuropathic pollakiuria, enuresis nocturna, dysmenorrhea, premenstrual tension, frigidity, mammalgia and impotence; dermal and oral diseases such as neuropathic dermatitis, pruritus cutaneus, atopic dermatitis, allergic dermatitis, chronic urticaria, eczema, abnormal salivation, aphthous stomatitis, toothache and grinding; and diseases of sense organs such as eye strain, glaucoma primarium, Meniere's syndrome, hearing impairment, tinnitus, giddiness, rhinitis and dysosmia.

Further, as apparently shown by the comparative tests with DPH, the pharmacological effects of the compounds of the present invention are utterly different from those of DPH and such effects could not be anticipated from effects of known compounds at all.

From a pharmacological viewpoint, among the compounds of the present invention, those in which the phenyl group at the 5-position of the hydantoin is substituted with halogen, $OR_7$ and/or, in some cases, with other substituents are preferred. Examples of the preferred compounds are listed below:

5-Alkyl-5-$OR_7$-substituted phenylhydantoins,
5-Heterocyclyl-5-$OR_7$-substituted phenylhydantoins,
5-Halogenophenyl-5-phenylhydantoins,
5-$OR_7$-Substituted phenyl-5-phenylhydantoins,
5,5-Bis($OR_7$-substituted phenyl)hydantoins,
5-(Halogeno-$OR_7$-substituted phenyl)-5-$OR_7$-substituted phenylhydantoins,
5-(Alkyl-$OR_7$-substituted phenyl)-5-$OR_7$-substituted phenylhydantoins,
5-(Di-$OR_7$-substituted phenyl)-5-$OR_7$-substituted phenylhydantoins, and
5,5-Bis(tri-$OR_7$-substituted phenyl)hydantoins.

As concrete examples of the above compounds, the following compounds may be mentioned:
5-Ethyl-5-(4-hydroxyphenyl)hydantoin,
5-Ethyl-5-(2-hydroxyphenyl)hydantoin,
5-(4-Hydroxyphenyl)-5-(2-thienyl)hydantoin,
5-(4-Fluorophenyl)-5-phenylhydantoin,
5-(2-Hydroxyphenyl)-5-phenylhydantoin,
5-(4-Hydroxyphenyl)-5-phenylhydantoin,
5,5-Bis(4-hydroxyphenyl)hydantoin,
5,5-Bis(3-hydroxyphenyl)hydantoin,
5,5-Bis(2-propoxyphenyl)hydantoin,
5-(3-Chloro-4-hydroxyphenyl)-5-(4-hydroxyphenyl)hydantoin,
5-(3-Chloro-4-methoxyphenyl)-5-(4-methoxyphenyl)hydantoin,
5-(4-Hydroxy-3-methylphenyl)-5-(4-hydroxyphenyl)hydantoin,
5-(4-Methoxy-3-methylphenyl)-5-(4-methoxyphenyl)hydantoin,
5-(3,4-Dihydroxyphenyl)-5-(4-hydroxyphenyl)hydantoin,
5,5-Bis(3,4,5-trihydroxyphenyl)hydantoin, and
5,5-Bis(3,4,5-trimethoxyphenyl)hydantoin.

As remedies, the compounds of the present invention can be used singly or in the form of an appropriate combination of some of them. The compounds can also be used in combination with other suitable medicines. The compounds can also be used in combination with suitable medical carriers or diluents. The compounds of the present invention may be given either perorally or non-perorally and they can be prescribed by conventional methods.

They can be prescribed in capsules, tablets, pills, powders and granules to be given perorally. The compounds of the present invention can be mixed with at least one vehicle such as sucrose, lactose, starch or carboxymethylcellulose for the preparation thereof.

Further, the preparations may contain ordinary additives, other than said vehicles, such as lubricants, for example, stearic acid salts and talc, binders, for example, dextrin, crystalline cellulose and acacia gum, disintegrators and/or coating agents, if necessary. Further, if desired, flavors and/or sweetening agents may be incorporated therein.

Another form of the preparation is a syrup, i.e. the compound is dissolved in a sucrose solution.

As non-peroral preparations, there may be mentioned sterilized aqueous or non-aqueous solutions for injection. The preparations of this type may contain adjuvants such as isotonizing agents, antiseptics, solubilizers and stabilizers. The preparations can be subjected to sterilization treatments such as filtration, introduction of a sterilizer, sterilizing irradiation or heating the compositions. The preparations of this type may be made in the form of a sterilized solid composition which is to be dissolved in sterilized water or a sterilized injection medium before use.

As other non-peroral preparations, there may be mentioned suppositories and ointments made by mixing the compounds with suitable bases.

The amount of the compoud of the present invention to be contained in the composition may be varied suitably, but it must be determined so as to obtain a suitable dosage. The dosage is variable according to the desired treatment effect, route of administration, subject and period of treatment. Generally, for adults, peroral administration of 1–5,000 mg/day of the compounds of the present invention or non-peroral administration of 0.1–1,000 mg/day thereof is preferable. The desired effects can be obtained by administration of one to several units/day of a peroral preparation containing 1–500 mg of the compounds of the present invention or a non-peroral preparation containing 0.1–300 mg thereof.

Examples of pharmaceutical formulations containing the compounds of the present invention as active ingredients will be given below, which by no means limits the invention.

(i) Tablets:

A typical example of tablets containing 50 mg of a compound of the present invention is given below:

| | Components | Amount (mg)/tablet |
|---|---|---|
| (a) | 5-(3-chloro-4-methoxyphenyl)- 5-(4-methoxyphenyl)hydrantoin | 50.0 |
| (b) | lactose | 106.0 |
| (c) | crystalline cellulose | 30.0 |
| (d) | calcium carboxymethylcellulose | 10.0 |
| (e) | magnesium stearate | 4.0 |
| | Total | 200.0 mg |

Above components (a) through (d) are equally mixed together. The mixture is kneaded together with water used as the granulation medium. The mixture is shaped into granules by a granulating machine having a 20 mesh screen. The granules are dried with warm air. Thus dried granules are passed through a 14 mesh sieve, then mixed with component (e) and shaped into tablets by a proper tablet machine.

(ii) Capsules:

Examples of capsules containing 50 mg and 100 mg of a compound of the present invention per capsule are given below:

| | Components | Amount (mg)/capsule | |
|---|---|---|---|
| (a) | 5,5-bis(3,4,5-trihydroxyphenyl)- hydantoin | 50.0 | 100.0 |
| (b) | lactose | 251.7 | 231.5 |
| (c) | potato starch | 129.0 | 99.2 |
| (d) | magnesium stearate | 4.3 | 4.3 |
| | Total | 435 mg | 435 mg |

The above components are equally mixed together and charged in hard capsules.

(iii) Injections:

An example of injections containing 1 mg of a compound of the present invention per one ampoule (1 ml.) is given below:

| | Components | Amount/ampoule |
|---|---|---|
| (a) | 5,5-bis(4-hydroxyphenyl)hydantoin | 1 mg |
| (b) | Sodium chloride | proper amount |
| (c) | Water for injection | " |
| (d) | Solubilizer | " |
| | Total | 1 ml. |

The above components are mixed together to form a solution, which is then filtered and charged in a 1 ml. ampoule. The ampoule is closed by fusion and sterilized.

What is claimed is:

1. A hydantoin derivative of the general formula:

in which:
(a) when $R_1$ is hydroxy, and each of $R_2$ and $R_3$ is independently hydrogen,
X is $C_1$–$C_3$ alkyl, thienyl, or hydroxyphenyl;
(b) when $R_1$ is $C_1$–$C_3$ alkoxy, $R_2$ is halogen, and $R_3$ is hydrogen,
X is $C_1$–$C_3$ alkoxyphenyl; and
(c) when each of $R_1$, $R_2$ and $R_3$ is independently hydroxy,
X is trihydroxyphenyl p1 or a pharmaceutically acceptable salt thereof.

2. The hydantoin derivative as claimed in claim 1 wherein $R_1$ is hydroxy, each of $R_2$ and $R_3$ is independently hydrogen, and X is $C_1$–$C_3$ alkyl.

3. The hydantoin derivative as claimed in claim 2 wherein the alkyl is ethyl.

4. The hydantoin derivative as claimed in claim 1 wherein $R_1$ is hydroxy, each of $R_2$ and $R_3$ is independently hydrogen, and X is thienyl.

5. The hydantoin derivative as claimed in claim 1 wherein $R_1$ is hydroxy, each of $R_2$ and $R_3$ is independently hydrogen, and X is hydroxyphenyl.

6. The hydantoin derivative as claimed in claim 5 wherein the derivative is 5,5-bis(4-hydroxyphenyl)-hydantoin.

7. The hydantoin derivative as claimed in claim 1 wherein $R_1$ is $C_1$–$C_3$ alkoxy, $R_2$ is halogen, $R_3$ is hydrogen, and X is $C_1$–$C_3$ alkoxyphenyl.

8. The hydantoin derivative as claimed in claim 7 wherein the $C_1$–$C_3$ alkoxy is methoxy.

9. The hydantoin derivative as claimed in claim 1 wherein the derivative is 5, 5-bis(3,4,5-trihydroxyphenyl) hydantoin.

10. A pharmaceutical composition for the teatment of stress containing an effective amount of a compound of claim 1 which is a sedative and a suitable carrier.

11. A pharmaceutical composition for the treatment of stress containing an effective amount of a compound of claim 1 which is an analgesic and a suitable carrier.

12. A pharmaceutical composition for the treatment of stress containing an effective amount of a compound of claim 1 which is an antiulcerogenic agent and a suitable carrier.

13. A pharmaceutical composition for the treatment of stress containing an effective amount of a compound of claim 1 which is a hypnotic and a suitable carrier.

14. A pharmaceutical composition for the treatment of stress containing an effective amount of a compound of claim 1 which is an antihypertensive drug and a suitable carrier.

15. A pharmaceutical composition containing a compound of claim 1 which is a peroral preparation comprising 1-500 mg of the compound of the general formula shown and a pharmaceutically acceptable carrier.

16. A pharmaceutical composition of claim 15 of which pharmaceutically acceptable carrier is selected from the group consisting of sucrose, lactose, starch and carboxymethylcellulose.

17. A pharmaceutical composition of claim 15 which is in the form of tablets or capsules.

18. A pharmaceutical composition containing an effective amount of a compound of claim 1 which is a non-peroral prepration comprising 0.1-300 mg of a compound of general formula shown and pharmaceutically acceptable diluent.

19. A pharmaceutical composition of claim 18 of which pharmaceutically acceptable diluent is selected from the group consisting of water for injection or isotonic sodium chloride solution.

20. A pharmaceutical composition of claim 18 which is in the form of injections.

21. The method for reducing stress iin a human being which comprises administering to the human being a compound as set forth in any one of claims 1 to 9 in an amount effective to reduce stress.

22. A pharmaceutical composition for the treatment of stress said pharmaceutical composition containing a stress reducing amount of a derivative set forth in claim 1.

* * * * *